US006051594A

United States Patent [19]
Lowrey

[11] Patent Number: 6,051,594
[45] Date of Patent: *Apr. 18, 2000

[54] METHODS AND FORMULATIONS FOR MODULATING THE HUMAN SEXUAL RESPONSE

[75] Inventor: Fred Lowrey, Lincoln, Nebr.

[73] Assignee: Zonagen, Inc., The Woodlands, Tex.

[*] Notice: This patent is subject to a terminal disclaimer.

[21] Appl. No.: 09/362,825

[22] Filed: Jul. 28, 1999

Related U.S. Application Data

[63] Continuation of application No. 08/959,672, Oct. 29, 1997, Pat. No. 5,981,563, which is a continuation-in-part of application No. 08/431,145, Apr. 28, 1995, Pat. No. 5,731,339.

[51] Int. Cl.$^7$ .................................................. A61K 31/415
[52] U.S. Cl. ......................................................... 514/400
[58] Field of Search ............................................. 514/400

[56] References Cited

U.S. PATENT DOCUMENTS

| | | | |
|---|---|---|---|
| 2,503,059 | 4/1950 | Miescher et al. | 260/309.6 |
| 3,937,834 | 2/1976 | Hunger et al. | 424/273 |
| 3,943,246 | 3/1976 | Sturmer | 424/177 |
| 4,127,118 | 11/1978 | Latorre | 128/79 |
| 4,139,617 | 2/1979 | Grunwell et al. | 424/238 |
| 4,530,920 | 7/1985 | Nestor et al. | 514/15 |
| 4,801,587 | 1/1989 | Voss et al. | 514/248 |
| 4,863,911 | 9/1989 | Anderson, Jr. et al. | 514/176 |
| 4,885,173 | 12/1989 | Stanley et al. | 424/440 |
| 5,059,603 | 10/1991 | Rubin | 514/264 |
| 5,065,744 | 11/1991 | Zusmanovsky | 128/79 |
| 5,079,018 | 1/1992 | Ecanow | 426/385 |
| 5,145,852 | 9/1992 | Virag | 514/253 |
| 5,236,904 | 8/1993 | Gerstenberg et al. | 514/12 |
| 5,256,652 | 10/1993 | El-Rashidy | 514/58 |
| 5,270,323 | 12/1993 | Milne, Jr. et al. | 514/309 |
| 5,298,261 | 3/1994 | Pebley et al. | 424/488 |
| 5,399,581 | 3/1995 | Laragh et al. | 514/396 |
| 5,565,466 | 10/1996 | Gioco et al. | 514/248 |
| 5,731,339 | 3/1998 | Lowrey | 514/400 |

FOREIGN PATENT DOCUMENTS

| | | |
|---|---|---|
| 1059914 | 8/1979 | Canada . |
| 1063516 | 10/1979 | Canada . |
| 1246446 | 12/1988 | Canada . |
| 0 357 581 | 3/1990 | European Pat. Off. . |
| 191068 | 3/1982 | New Zealand . |
| WO 95/05172 | 2/1995 | WIPO . |

OTHER PUBLICATIONS

*ABPI Data Sheet Compendium*, pp. 186–187 (1976).
*ABPI Data Sheet Compendium*, pp. 186–189 (1977).
AC–Di–Sol®, Croscarmellose Sodium, NF (Accelerates DisSolution) (Product Description Brochure); FMC Corporation, Philadelphia, PA, pp. 1–9 (1988).
Althof et al., "Sexual, psychological, and marital impact of self–injection of papaverine and phentolamine: a long–term prospective study," *J. Sex & Marital Ther.*, 17(2):101–112 (1991).
Azadzoi, K.M. et al., "Effects of Intracavernosal Trazadone Hydrochloride: Animal and Human Studies," *J. Urology*, 144(5):1277–1282 (Nov., 1990).
Barnett et al., "The Action of "Regitine" in Man with Special Reference to its Adrenergic Blocking Action," *Australasian Anals of Medicine*, 1:109–119 (1952).
Beavo, J.A. et al., In: *Advances in Second Messenger and Phosphoprotein Research*, Greengard et al., (eds.), vol. 22, pp. 1–38 (1988).
Becker, A.J. et al., "Oral Phentolamine as Treatment for Erectile Dysfunction," *The Journal of Urology*, 159:1214–1216 (1998).
*Biotechnology Newswatch*, "Nice try, but no Viagra, say experts reviewing new potency pills," pp. 4–5 (Jun., 1998).
Brindley, G.S., "Cavernosal alpha–blockade and human penile erection," *J. Physiol.*, 342:24P (1983).
Brindley, G.S., "Cavernosal Alpha–Blockade: A New Technique for Investigating and Treating Erectile Impotence," *Brit. J. Psychiat.*, 143:332–337 (1983).
Brindley, G.S., "Pilot experiments on the actions of drugs injected into the human corpus cavernosum penis," *Br. J. Pharmac.*, 87:495–500 (1986).
*British Pharmaceutical Codex 1954*, London, The Pharmaceutical Press, 17 Bloomsbury Square WC1, pp. 572–575.
*British Pharmaceutical Codex 1959*, London, The Pharmaceutical Press, 17 Bloomsbury Square WC1, pp. 562–565.
*British Pharmaceutical Codex 1968*, London, The Pharmaceutical Press, 17 Bloomsbury Square WC1, pp. xxiv–xxvii and 616–619.
*British Pharmaceutical Codex 1973*, London, The Pharmaceutical Press, 17 Bloomsbury Square WC1A 2NN, pp. 373–374.
*British Pharmacopceia 1980*, vol. I, London Her Majesty's Stationary Office 1980, p. 344.
*British Pharmacopœia 1963*, The Pharmaceutical Press 17 Bloomsbury Square London WC1, pp. 600–603.
*British Pharmacopœia 1968*, The Pharmaceutical Press 17 Bloomsbury Square London WC1, pp. 758–761.
*British Pharmacopœia 1973*, London Her Majesty's Stationary Office 1973, p. 364.
*British Pharmacopcœia 1980*, vol. II, London Her Majesty's Stationary Office 1980 (see attached—one page).
*British Pharmacopœia 1988*, vol. I, London Her Majesty's Stationary Office, pp. 434–435.
*British Pharmacopœia 1988*, vol. II, London Her Majesty's Stationary Office, p. 835.
Corriere, J.N. Jr. et al., "Development of Fibrotic Penile Lesions Secondary to the Intracorporeal Injection of Vasoactive Agents," *J. Urology*, 140:615–617 (1988).

(List continued on next page.)

Primary Examiner—Phyllis G. Spivack
Attorney, Agent, or Firm—Marshall, O'Toole, Gerstein, Murray & Borun

[57] ABSTRACT

The invention is directed to improved methods for modulating the human sexual response by orally administering a formulation of the vasodilator phentolamine to the blood circulation and thereby modulating the sexual response on demand.

101 Claims, No Drawings

OTHER PUBLICATIONS

Dawson, A. et al., "The Transient Anti–Hypertensive Effect of Phentolamine in Patients Receiving Beta–Blocker Treatment," *J. Int. Med. Res.*, 5:462–464 (1977).

Dhar, S.K. et al., "Clinical management of hypertensive emergencies," *Heart Lung*, 5(4):571–575 (Jul./Aug., 1976).

Diedrichs, W. et al., "Reduction of Sympathetic Influence on Penile Erection by Phentolamine," *Urol. Int.*, 46:64–66 (1991).

Finkbeiner, A.E. et al., "Uropharmacology XI. Adrenergic–Blocking Agents and Drugs Affecting Catecholamine Binding and Release," *Urology*, 8(6):693–700 (Jun., 1979).

*French Pharmaceutical Compendium*, p. 1178 (1969).

*French Pharmaceutical Compendium*, pp. 1704–1705 (1964).

*French Pharmaceutical Compendium*, pp. 1802–1803 (1965).

Georgopoulos, A.J. et al., "Treatment of Chronic Heart Failure with Slow Release Phentolamine," *Europ. J. Clin. Pharmacol.*, 13:325–329 (1978).

*German Drug Compendium*, pp. 1028–1029 (1969).

*German Drug Compendium*, pp. 1054–1055 (1971).

Gissinger, D. et al., "A Comparative Evaluation of the Properties of Some Tablet Disintegrants," *Drug Development and Industrial Pharmacy*, 6(5):511–536 (1980).

Godbillion et al., "Determination of the Major Metabolite of Phentolamine in Human Plasma And Urine By High–Performance Liquid Chromatography," *J. Chromatography*, 222:461–466 (1981).

Gould, L.A. et al., "Oral Therapy with Phetolamine in Chronic Congestive Heart Failure," *Chest*, 75(4):487–491 (Apr., 1979).

Gwinup, G., "Oral Phentolamine in Nonspecific Erectile Insufficiency," *Ann. Int. Med.*, 109(2):162–163 (Jul., 1998).

Imhof, P.R. et al., "Human Pharmacology of Orally Administered Phentolamine," In: *Phentolamine in Heart Failure and Other Cardiac Disorders*, Taylor, S.H., and Gould, L.A., (eds.), Ben Huber, pp. 11–22 (1976).

Johnson, B.F. et al., "A controlled trial of oxprenolol and oral phentolamine in the management of hypertension," In: *Hypertension—its nature and treatment.* Burley, D.M. et al., (eds.). An international symposium, Malta, Oct. 18–21 1974. Horsham England, CIBA Laboratories, pp. 259–268 (1975).

Kersting, F. et al., "Clinical Pharmacology of Prazosin and Phentolamine in Patients with Heart Failure," *J. Cardiovascular Pharmacology*, 2(Suppl. 3):S373–S383 (1980).

Larsen et al., "Fibrosis of Corpus Cavernosum after Intracavernous Injection of Phentolamine/Papaverine," *J. Urology*, 137:292–293 (Feb., 1987).

Marriot, H.J.L., "An Alarming Pressor Reaction To Regitine," 46(5):1001–1002 (May, 1957).

McCleane, G.J., "Oral Phentolamine Mesylate in the treatment of Complex Regional Pain Syndrome," *The Ulster Medical Journal*, 65(1):87–88 (May, 1996).

McDonnell, S.M. et al., "Imipramine–induced Erection, Masturbation, and Ejaculation in Male Horses," *Pharmacol. Biochem. Behav.* (USA), 27(1):187–191 (May, 1987) (Abstract).

Montorsi, F. et al., "Clinical Reliability of Multi–Drug Intracavernous Vasoactive Pharmacotherapy for Diabetic Impotence," *Acta Diabetol.*, 31:1–5 (1994).

Montorsi, F. et al., "Pharmacological Management of Erectile Dysfunction," *Drugs*, 50(3):465–479 (1995).

NIH Consensus Conference, "Impotence," NIH Consensus Development Panel on Impotence, *Journal American Medical Association*, 270(1):83–90 (1993).

Parte I Specialità Medicinali E Riferimenti Ad Altri Reparti Secondo Ordine Alfabetica, Italian Drug Compendium (L 'Infromatore Farmaceutico) pp. 1, 535, and 753 (1979).

Parte I Specialità Medicinali, Italian Drug Compendium (L 'Informatore Farmaceutico), pp. 1 and 551 (1975).

Parte I Specialità Medicinali, Italian Drug Compendium (L 'Informatore Farmaceutico), pp. 3 and 486 (1969).

Pfister et al., "Estimation of the Plasma Concentration and Course of Action of Phentol–amine Based On Its Inhibitory Effect On Adrenaline–Induced Platelet Aggregation," *Br. J. Clin. Pharmac.*, 5:175–180 (1978).

*Phyicians' Desk Reference*, 37 Edition, pp. 409 and 864 (1983).

Ruskin, J.N. et al., "Primary Pulmonary Hypertension Treated With Oral Phentolamine," *Annals of Internal Medicine*, 90:772–774 (1979).

Sioufi, A. et al., "Gas Chromatographic Determination of Phenentolamine (Regitine) in Human Plasma and Urine," *Journal of Chromatography*, 222:429–435 (1981).

Sjöstrand, N.O. et al., "Principle mechanisms controlling penile retraction and protrusion in rabbits," *Acta Physiol. Scand.*, 106(2):199–241 (Jun., 1979).

Sonda, L.P. et al., "The Role of Yohimbine for the Treatment of Erectile Impotence," *J. Sex & Marital Ther.*, 16(1):15–21 (1990).

Taylor, S.H., "Vasodilator Drugs in the Treatment of Heart Failure," *J. Cardiovascular Pharmacology*, 2 (Suppl. 3):S407–S425 (1980).

Terrett, N.K. et al., "Sildenafil (VIAGRA™), A Potent and Selective Inhibitor of Type 5 cGMP Phosphodiesterase with Utility for the Treatment of Male Erectile Dysfunction," *Bioorgnic & Medicinal Chemistry Letters*, 6(15):1819–1824 (1996).

The Extra Pharmacopoeia: The authoritative reference work on drugs and medicines in current use, Twenty–sixth Edition, 2 pages (1988).

*The Pharmacopeia of the United States of America* (The United States Pharmacopeia), Fifteenth Revision, U.S.P. XV, By authority of The United States Pharmaceutical Convention, Inc., meeting at Washington, D.C., May 9 and 10, 1950, Prepared by the Committee of Revision and published by the Board of Trustees, Official from Dec. 15, 1955, pp. 936–939 and 540–543.

*The Merck Index*, Eighth Edition, Merck & Co., Inc., New Jersey, USA, p. 814 (1968).

Saeed, M. et al., "α–Adrenoceptor Blockade by Phentolamine Causes β–Adrenergic Vasodilation by Increased Catecholamine Release Due to Presynaptic α–Blockade," *Journal of Cardiovascular Pharmacology*, 4:44–52 (1982).

Schreiber, R. et al., "Hemodynamic Improvement following a Single Dose of Oral Phentolamine: Administration in Patients with Chronic Low Output Cardiac Failure," *Chest*, 76(5):571–575 (Nov., 1979).

Selvaag, O. et al., "Experiences with Regitin (A New Vasodilator Compound)," *Acta Medica Scandinavica*, vol. CXLVI, fase. III, pp. 209–215 (1953).

*The Merck Index*, Ninth Edition, Merck & Co., Inc., New Jersey, USA, p. 945 (1976).

*The Merck Index of Chemicals and Drugs*, Seventh Edition, Merck & Co., Inc., New Jersey, USA, p. 799 (1960).

*The Merck Index*, Tenth Edition, Merck & Co., Inc., New Jersey, USA, pp. 1047–1048 (1983).

*The Merck's Index,* Fourth Edition, Merck & Co., Inc., New Jersey, U.S.A., p. 392 (1930).

Trapold, J.H. et al., "Pharmacological and Toxicological Studies on 2-(N-p'tolyl-N-(m'-Hydroxyphenyl)-Aminomethyl)-Imidazoline (C-7337), A New Adrenergic Blocking Agent," in Joseph Hugh Trapold Thesis (M.S.)—University of Tennessee, Memphis, pp. 119–127 (1950).

*United States Pharmacopeia,* Twentieth Revision, Official from Jul. 1, 1980, The National Formulary, Fifteenth Edition, Official from Jul. 1, 1980, United States Pharmacopeial Convention, Inc., Rockville, Maryland, pp. 615–617 (1979).

Virag, R. et al., "Intracavernous Injection of Papaverine as a Diagnostic and Therapeutic Method in Erectile Failure," *Angiology,* 35:79–87 (1984).

Virag, R., "Intracavernous Injection of Papaverine for Erectile Failure," *Lancet,* ii:938 (1982).

Von Hippel, F.A., "Solution to a Conservation Problem," *Science,* 281:1805–1806 (Sep., 1998).

Wagner, G. et al., "Buccal Phentolamine–A pilot trial for male erectile dysfunction at three separate clinics," *Int. J. Impotence Res.,* 6(Suppl.1):D78 (1994).

Williams, in *Textbook of Endocrinology,* p. 313 (Circa, 1976).

Zorgniotti, A.W., ""On Demand" Oral Drug For Erection In Impotent Men," *J. Urology* (AUA Eighty–Seventh Annual Meeting May 10–14, 1992), 147(4)(Suppl.):308A (Apr., 1992) (Abstract 382).

Zorgniotti et al., "Auto–Injection of the Corpus Cavernosum with a Vasoactive Drug Combination for Vasculogenic Impotence," *J. Urol.,* 133:39–41 (1985).

Zorgniotti, "Experience with Buccal Phentolamine Mesylate for Impotence," *International Journal of Impotence Research,* 6(1):37–41 (Mar., 1994).

METHODS AND FORMULATIONS FOR MODULATING THE HUMAN SEXUAL RESPONSE

CROSS REFERENCE TO RELATED APPLICATION

This application is a continuation of U.S. patent application Ser. No. 08/959,672 filed Oct. 29, 1997, U.S. Pat. No. 5,981,563, which is a continuation-in-part of U.S. patent application Ser. No. 08/431,145, filed on Apr. 28, 1995, U.S. Pat. No. 5,731,339, and from which this application claims priority.

FIELD OF THE INVENTION

The application is directed to improved formulations for the administration of vasodilator agents to the blood circulation of a human in order to modulate the human sexual response on demand.

BACKGROUND OF THE INVENTION

The human sexual response in both males and females results from a complex interplay of psychological, hormonal, and other physiological influences. One important aspect of human sexual response that is common to both men and women is the erectile response which itself results from an interplay between the autonomic nervous system, the endocrine system, and the circulatory system.

Failure of the erectile response is most common in men and is referred to as impotence. Impotence is the inability of a male to achieve or sustain a penile erection sufficient for vaginal penetration and intercourse. Numerous approaches have been taken in attempts to treat impotence. These approaches include the use of external or internally implanted penile prosthesis. (See, e.g., U.S. Pat. No. 5,065,744, to Zumanowsky). A variety of drugs and methods for administering drugs have also been used in attempts to treat impotence. For example, U.S. Pat. No. 3,943,246 to Stürmer addresses treatment of impotence in men by buccal and peroral administration of daily doses of 300–1500 international units (I.U.) of oxytocin or daily divided doses of 150–250 I.U. of desamino-oxytocin. The patent states that the buccal administration of 100 I.U. three times a day for 14 days results in improvement of impotentia erectionis in 12 of the 16 patients treated.

U.S. Pat. No. 4,530,920 to Nestor et al. suggests the possibility that administration of nonapeptide and decapeptide analogs of luteinizing hormone releasing hormone agonists may be useful in the induction or enhancement of sexual behavior or therapy for impotence or frigidity. Nestor et al. suggest numerous routes of administration of the analogs including buccal, sublingual, oral, parenteral (including subcutaneous, intramuscular, and intravenous administration), rectal, vaginal, and others.

U.S. Pat. No. 4,139,617 to Grunwell et al. suggests buccal and other routes of administration of 19-oxygenated-androst-5-enes for the endocrine mediated enhancement of the libido in humans.

U.S. Pat. No. 4,863,911 to Anderson et al. addresses methods for treating sexual dysfunction in mammals using a biooxidizable, blood-brain barrier penetrating estrogen derivative. One of the purported objects of the Anderson et al. invention is the treatment of "psychological impotence" in males. Test results showed that the drugs used in the study stimulated mounting behavior, intromission, and mount latency in castrated rats.

A number of publications have proposed the use of various vasodilators for the treatment of impotence in males. Attempts to utilize vasodilators for the treatment of impotence were prompted by the fact that a significant percentage of cases of impotence were noted to be vasculogenic, i.e. resulting from vascular insufficiency.

Voss et al., U.S. Pat. No. 4,801,587, issued Jan. 31, 1989, addresses the use of an ointment containing a vasodilator and a carrier agent for topical application to the penis of impotent men. The Voss et al. patent also describes application of such an ointment into the urethra of the penis using a catheter as well as a multi-step regimen for applying a vasodilator to the skin of the penis. In addition, Voss et al. proposes the surgical removal of a portion of the fibrous sheath surrounding the corpora cavernosum, thereby facilitating the penetration of a vasodilator-containing ointment into the corpora cavernosum. Vasodilators suggested for use by Voss et al. include papaverine, hydralazine, sodium nitroprusside, phenoxybenzamine, and phentolamine. The Voss et al. patent, however, provides no information regarding the actual efficacy of the treatments proposed or the nature of the response to such treatments.

U.S. Pat. No. 4,127,118 to Latorre describes treating male impotence by direct injection of the vasodilating drugs into the corpus cavernosum and the corpus spongiosum of the penis using a syringe and one or more hypodermic needles. More particularly, the Latorre patent proposes the intracavernosal and intraspongiosal injection of sympathomimetic amines such as nylidrin hydrochloride, adrenergic blocking agents such as tolazoline hydrochloride, and direct acting vasodilators such as isoxsuprine hydrochloride and nicotinyl alcohol.

Brindley, G. S. (*Br. J. Pharmac.* 87:495–500, 1986) showed that, when injected directly into the corpus cavernosum using a hypodermic needle, certain smooth muscle relaxing drugs including phenoxybenzamine, phentolamine, thymoxamine, imipramine, verapamil, papaverine, and naftidrofuryl caused erection. This study noted that injection of an "appropriate dose of phenoxybenzamine or papaverine is followed by an unrelenting erection lasting for hours." Injection of the other drugs studied induced erections lasting from about 11 minutes to about 6.5 hours.

Zorgniotti et al., *J. Urol.* 133:39–41 (1985) demonstrated that the intracavernosal injection of a combination of papaverine and phentolamine could result in an erection in otherwise impotent men. Similarly, Althof et al. *J. Sex Marital Ther.* 17(2): 101–112 (1991) reported that intracavernosal injection of papaverine hydrochloride and phentolamine mesylate resulted in improved erectile ability in about 84% of patients injected. However, in that study the dropout rate was 57%, fibrotic nodules developed in 26% of the patients, 30% of the patients developed abnormal liver function values, and bruising occurred in 19% of the patients.

Other studies describing intracavernosal injection of drugs using hypodermic needles for the treatment of impotence include: Brindley, *J. Physiol.* 342:24P (1983); Brindley, *Br. J. Psychiatr.* 143:312–337 (1983); Virag, *Lancet* ii:978 (1982); and Virag, et al., *Angiology* 35:79–87 (1984).

While intracavernosal injection may be useful for inducing erections in impotent men, the technique has numerous drawbacks. Obvious drawbacks include pain, risk of infection, inconvenience and interference with the spontaneity of the sex act. Priapism (prolonged and other painful erection) also appears to be a potential problem when using injection methods. See, e.g. Brindley, (1986). Another problem arising in some cases of intracavernosal injection involves the formation of fibrotic lesions in the penis. See, e.g., Corriere, et al., *J. Urol.* 140:615–617 (1988) and Larsen, et al., *J. Urol.* 137:292–293 (1987).

Phentolamine, which has been shown to have the potential to induce erection when injected intracavernosally, has also been the subject of oral administration to test its effects in men having non-specific erectile insufficiency (Gwinup, *Ann. Int. Med.* Jul. 15, 1988, pp. 162–163). In that study, 16 patients ingested either a placebo or a 50 mg orally administered dose of phentolamine. Eleven of the 16 patients (including three placebo-treated patients) became tumescent, became more responsive to sexual stimulation, and were able to achieve an erection sufficient for vaginal penetration after waiting 1.5 hours to attempt intercourse.

Sonda et al. *J. Sex & Marital Ther.* 16(1): 15–21 (year) reported that yohimbine ingestion resulted in subjective improvement in erectile ability in 38% of impotent men treated, but only 5 % of the treated patients reported complete satisfaction.

Zorgniotti et al, PCT/US94/09048, describes the transmucosal administration of a variety of vasodilators including phentolamine mesylate for modulating the human sexual response.

Of interest to the background of the invention is the disclosure of Stanley et al., U.S. Pat. No. 4,885,173, which addresses methods administering drugs having cardiovascular or renal vascular activity through use of a lollipop assertedly facilitating drug absorption through the mucosal tissues of the mouth, pharynx, and esophagus. The Stanley et al. patent proposes that a large number of lollipop-administered drugs may improve cardiovascular function including drugs exhibiting direct vasodilating effects, including calcium channel blockers, β-adrenergic blocking agents, serotonin receptor blocking agents, angina blocking agents, other anti-hypertensive agents, cardiac stimulating agents, and agents which improve renal vascular function.

U.S. Pat. No. 5,059,603 to Rubin describes the topical administration to the penis of isoxsuprine and caffeine, and nitroglycerine and caffeine along with suitable carrier compounds for the treatment of impotence.

There continues to exist a need in the art for effective means for modulating human sexual response and especially for enhancing erectile ability in males suffering from impotence. Ideally, such means would be convenient and simple to use, would not require a constant dosage regimen or even multiple doses to achieve desired results, would be non-invasive and would allow a rapid and predictable capacity for onset of erectile function on demand and in response to normal sexual stimulation.

All of the references set out in this specification are incorporated herein by reference in their entirety.

SUMMARY OF THE INVENTION

The present invention provides improved formulations for modulating the human sexual response in a human by administering a vasodilator agent to the circulation in an amount effective to increase blood flow to the genitalia. According to the invention, modulation of male and female human sexual response is provided on demand by administering an effective vasodilating amount of the agent in an oral formulation. Vasodilating agents useful in the present invention include, but are not limited to, the group consisting of phentolamine mesylate, phentolamine hydrochloride, phenoxybenzamine, yohimbine, organic nitrates (e.g. nitroglycerin), thymoxamine, imipramine, verapamil, isoxsuprine, naftidrofuryl, tolazoline and papaverine. The presently preferred vasodilator agent is phentolamine mesylate. The presently preferred oral formulation comprises in combination, a vasodilator agent in a rapidly dissolving tablet. Preferred rapidly dissolving tablets have a disintegration time of from about 1 minute to about 10 minutes. Most preferred are rapidly dissolving tablets having the disintegration times of less than one minute. Preferred oral doses of phentolamine mesylate in the formulations of the present invention are from about 5 mg to about 80 mg.

The present invention is also directed to a vasodilator formulation comprising in combination, a vasodilator and a chewable tablet.

The present invention is specifically directed to improved methods for treating male impotence, by administering a vasodilator agent in an amount effective to increase blood flow to the penis wherein erectile ability on demand is permitted by oral administration of the vasodilator.

Preferably, the amount of vasodilating agent used in the practice of the invention for treatment of male impotence is effective to improve erectile ability in from about 1 minute to about 60 minutes following administration of the agent.

The invention is also specifically directed to methods for modulating the excitation and plateau phases of the female sexual response on demand by oral administration of an effective amount of vasodilator agent.

The methods of the present invention are also useful in preparation for sexual intercourse by virtue of the ability to modulate the sexual response in both males and females.

The present invention is also directed to the use of a drug having vasodilator activity for the manufacture of a medicament for oral administration to modify, on demand, the sexual response in a human and more particularly to improve erectile ability in response to sexual stimulation. Vasodilator drugs useful for manufacturing the medicament include, but are not limited to, phentolamine mesylate, phentolamine hydrochloride, phenoxybenzamine yohimbine, organic nitrates, thymoxamine, imipramine, verapamil, isoxsuprine, naftidrofuryl, tolazoline, and papaverine.

Numerous other advantages of the present invention will be apparent from the following detailed description of the invention including the accompanying examples and the appended claims.

DETAILED DESCRIPTION

The human sexual response in both the male and female involves a complex interplay between endocrine, neurological and psychological components which result in certain physiological and anatomical responses in both men and women.

While there are obvious differences in the sexual response between men and women, one common aspect of the sexual response is the erectile response. The erectile response in both males and females is result of engorgement of the erectile tissues of the genitalia with blood in response to sexual stimulation (physical, psychological, or both).

The vasculature which serves erectile tissue in both men and women is similar. In particular, in both men and women, the arterial circulation to the erectile tissues of the genitalia derives from the common iliac artery which branches from abdominal aorta. The common iliac artery bifurcates into the internal and external iliac arteries. The internal pudic artery arises from the smaller of two terminal branches of the anterior trunk of the internal iliac artery. In the female, the internal pudic artery branches into the superficial perineal artery which supplies the labia pudenda. The internal pudic artery also branches into the artery of the bulb which supplies the bulbi vestibuli and the erectile tissue of the vagina. The artery of the corpus cavernosum, another branch of the internal pudic artery supplies the cavernous body of the clitoris. Still another branch of the internal pudic artery is the arteria dorsalis clitoridis which supplies the dorsum of the clitoris and terminates in the glans and membranous folds surrounding the clitoris which correspond to the prepuce of the male.

In the male, the internal pudic artery branches into the dorsal artery of the penis (which itself branches into a left and right branch) and the artery of the corpus cavernosum, all of which supply blood to the corpus cavernosum. The dorsal artery of the penis is analogous to the artery dorsalis clitoridis in the female, while the artery of the corpus cavernosum in the male is analogous to the artery of the same name in the female.

The male erectile response is regulated by the autonomic nervous system which controls blood flow to the penis via the interaction of peripheral nerves associated with the arterial vessels in and around the corpus cavernosum. In the non-aroused or non-erect state, the arteries serving the corpus cavernosum are maintained in a relatively constricted state, thereby limiting the blood flow to the corpus cavernosum. However, in the aroused state, the smooth muscles associated with the arteries relax under the influence of catecholamines and blood flow to the corpus cavernosum greatly increases, causing expansion and rigidity of the penis. Brindley, supra (1986) hypothesizes that smooth muscle contraction opens valves through which blood can flow from the corpus cavernosum into the extracavernosal veins. According to Brindley (1986), when the relevant smooth muscles relax, the valves close diminishing venous outflow from the corpus cavernosum. When accompanied by increased arterial blood flow into the corpus cavernosum, this results in engorgement of the corpus cavernosum and an erection.

The pre-orgasmic sexual response in females can be broken down into distinct phases. Both the excitement phase and the plateau phase involve vasodilation and engorgement (vasocongestion) of the genitalia with arterial blood in a manner analogous to the male erectile response.

The excitement phase of the female sexual response is characterized by vasocongestion in the walls of the vagina which leads to the transudation of vaginal fluids and vaginal lubrication. Further, the inner one-third of the vaginal barrel expands and the cervix and the body of the uterus become elevated. This is accompanied by the flattening and elevation of the labia majora and an increase in clitoral size. [Kolodny et al., *Textbook of Sexual Medicine*, Little and Brown, Boston, Mass. (1979)].

The plateau phase follows the excitement phase in the female sexual response and is characterized by prominent vasocongestion in the outer one-third of the vagina, causing a narrowing of the opening of the vagina and a retraction of the shaft and the glans of the clitoris against the symphysis pubis. These responses are also accompanied by a marked vasocongestion of the labia. [Kolodny, supra (1979)].

The vasocongestive aspects of the female sexual response are not restricted to the genitalia in that areolar engorgement also occurs, sometimes to the extent that it masks the antecedent nipple erection that usually accompanies the excitement phase.

The failure of the erectile response in men to the extent that vaginal penetration and sexual intercourse cannot be achieved is termed impotence. Impotence has numerous possible causes which can be broken down into several general classifications. Endocrine related impotence can result from primary gonadal failure, advanced diabetes mellitus, hypothyroidism, and as one of the secondary sequelae of pituitary adenoma, idiopathic or acquired hypogonadism, hyperprolactinemia and other endocrine abnormalities.

Chronic systemic illnesses such as cirrhosis, chronic renal failure, malignancies and other systemic diseases can also cause impotence. Neurogenic impotence arising in the central nervous system can be caused by temporal lobe disorders caused by trauma, epilepsy, neoplasms and stroke, intramedullary spinal lesions, paraplegia, and demyelinating disorders. Neurogenic causes of impotence arising in the peripheral nervous system include somatic or autonomic neuropathies, pelvic neoplasms, granulomas, trauma, and others. Urologic causes of impotence include complete prostatectomy, local trauma, neoplasms, Peyronie's disease, and others. In addition, as discussed above, a significant percentage of cases of impotence are vasculogenic in nature.

As many as half the cases of male impotence may be psychogenic because there is no readily-ascertainable organic cause for the disorder. Even when there appears to be an underlying organic cause of impotence, psychologic factors may play a role in the disorder.

The present invention is designed to modify the circulatory aspects of the erectile response on demand using vasoactive agents administered to the circulation using a rapidly dissolving orally administered formulation.

A number of vasoactive agents may be used in the practice of the present invention based on demonstrated systemic efficacy as vasodilators. Useful vasodilating drugs include those generally classified as α-adrenergic antagonists, sympathomimetic amines and those agents which exhibit direct relaxation of vascular smooth muscle. Exemplary α-adrenergic antagonists include phentolamine, phentolamine hydrochloride, phentolamine mesylate, phenoxybenzamine, tolazoline, dibenamine, yohimbine, and others. Phentolamine mesylate is a preferred α-adrenergic agent vasodilator for use preferred practice of the present invention. An exemplary sympathomimetic amine contemplated for use in the method of the present invention is nylidrin and use of other sympathomimetic amines having vasodilating activity is also contemplated.

Nicotinic acid (or nicotinyl alcohol) has a direct vasodilating activity useful in the practice of the present invention. Also contemplated is the use of papaverine, a non-specific smooth muscle relaxant which possesses vasodilating activity and which has been used to treat male impotence by direct injection into the corpus cavernosum either alone or in combination with other drugs such as phentolamine. Organic nitrates such as nitroglycerine and amyl nitrate have pronounced vasodilating activity by virtue of their ability to relax vascular smooth muscle and are thus contemplated for use according to the invention. Other vasoactive drugs useful in the practice of the present invention include, without limitation, thymoxamine, imipramine, verapamil, naftidrofuryl, and isoxsuprine.

The formulations also eliminate the need for continuous therapy by providing a single dose for rapidly improving erectile ability on demand.

According to the present invention, the vasodilating agent is administered orally in the form of a rapidly dissolving tablet formulation, a rapidly dissolving chewable tablet formulation, solutions, effervescent formulations, and other orally administered formulations that permit the rapid introduction of the vasodilating substance to the circulation so as to improve erectile ability within a short time (on demand) after administration of a single dose of the agent.

Formulations and methods of the present invention are thus more convenient and help minimize any side-effects that may arise as a result of continuous or daily administration of the drugs. In addition, methods of the present invention allow more spontaneity in sexual activity than allowed by other methods such as the intracavernosal injection of vasodilators.

The examples set forth below are intended to be illustrative of the present invention and are not intended to limit the scope of the invention as set out in the appended claims. The invention is illustrated in the following examples with reference to phentolamine as a vasodilator and in particular, with reference to phentolamine mesylate.

Phentolamine can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention. Phentolamine can form pharmaceutically acceptable salts with organic and inorganic acids. Examples of suitable acids for salt formation are hydrohamic acids such as hydrochloric and hydrobromic; as well as other acids such as sulfuric, phosphoric, acetic, citric, oxalic, malonic, salicylic, malic, fumaric, succinic, ascorbic, maleic, methanesulfonic, toluenesulfonic, and other mineral and carboxylic acids known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base form for purposes of this invention. Phentolamine can also form crystalline polymorph forms or crystalline forms thereof using suitable or conventional crystallization procedures.

Example 1 describes rapidly dissolving formulations for the oral administration of vasodilating agents. Example 2 describes the bioavailability of phentolamine mesylate when administered using a rapidly dissolving oral formulation. Example 3 describes the effect of the administration of a rapidly dissolving oral formulation of phentolamine mesylate on male erectile ability. Example 4 describes other vasoactive agents useful in modulating the human sexual response. Example 5 addresses the practice of the present invention in modulating the erectile response in females.

EXAMPLE 1

Rapidly Dissolving Formulations for the Oral Administration of Vasodilating Agents The present invention is directed to rapidly dissolving orally administered formulations for the rapid delivery of vasodilating agents to the systemic circulation thereby allowing a rapid (on demand) onset of improved erectile ability in response to sexual stimulation. The invention is also directed to other orally administered formulations for "on demand" improvement in erectile ability in response to sexual stimulation including chewable tablets, effervescent formulations, solutions, lozenges, troches, powders, solutions, suspensions, emulsions, or encapsulated powders which, can be of the gelatin type or other types.

An exemplary formulation of a rapidly dissolving tablet that includes phentolamine mesylate is set out in Table 1.

TABLE 1

|  | mg/tablet |
|---|---|
| Phentolamine Mesylate, USP | 40 |
| Silicon Dioxide, NF | 8 |
| Stearic Acid, NF | 4 |
| Lactose, NF | 212 |
| Microcrystalline Cellulose, NF | 120 |
| Croscarmellose Sodium, NF | 16 |
| Total Tablet Weight | 400 |

The ingredients set out in Table 1 (and those used tablet formulations set out below) were finely divided and mixed thoroughly before being compression formed into tablets having a total weight of about 400 mg. Other methods of mixing and tablet formation will be readily apparent to those of skill in the art. Physical characteristics of the tablet prepared by this method include an average hardness of 10.7 Kp, an average thickness of about 0.20 inches and an average disintegration time of about 0.71 minutes.

As shown in Table 1, the disintegrant, croscarmellose sodium NF (available as Ac-Di-Sol®, from FMC Corporation) was used to accelerate the dissolution of the tablet although other disintegrants such as those described below may be used to achieve the same effect. Also encompassed by the present invention are vasodilators in pharmaceutically acceptable carriers which themselves disintegrate in about 20 minutes or less without the addition of a disintegrant.

Tablets useful in the practice of the present invention may include other pharmaceutical excipients, pharmaceutically acceptable salts, carriers, and other substances well known in the art. Buffering agents, flavoring agents, and inert fillers such as lactose, sucrose, corn starch, binders such as acacia, cornstarch, or gelatin. Disintegrants such as potato starch and analgetic acid as well as other commercially available disintegrants including Explotab® sodium starch glycolate, Polyplasdone XL® crospovidone NF, Starch 1500® pregelatinized starch NF. Gissinger et al., "A Comparative Evaluation of the Properties of Some Tablet Disintegrants", *Drug Development and Industrial Pharmacy* 6(5):511–536 (1980) also describes other disintegrants and methods for measuring disintegration time of tablets and is incorporated herein by reference. A method for measuring disintegration times of tablets is also set out in *European Pharmacopeia* 1980 which is also incorporated herein by reference. Preferred disintegration times for the practice of the present invention are less then about 20 minutes. More preferred are disintegration times of two minutes or less. Most preferred is a dissolution time of less than one minute. Preferred dissolution times may vary depending on the parmaco kinetic properties of the vasodilator agent itself.

Formulations useful in the practice of the present invention may vary so long as the formulation maintains the properties of rapid dissolution and improved bioavailability of the active ingredient or ingredients.

Another example of a rapidly disintegrating tablet formulation is described in U.S. Pat. No. 5,298,261 to Pebley et al., (the '261 patent) which is incorporated herein by reference. The '261 patent describes a rapidly dissolving tablet comprising a drug and a matrix network that has been vacuumdried below the equilibrium freezing point of the matrix but above its collapse temperature. The matrix network set out in the '261 patent preferably includes a gum, a carbohydrate, and the drug. Preferred gums include acacia, guar, xanthin, carrageenan, or tragacanth. Preferred carbohydrates described in the '261 patent include mannitol, dextrose, sucrose, lactose, maltose, maltodextrin, or corn syrup solids.

Another rapidly dissolving formulation is described in U.S. Pat. No. 5,079,018 to Ecanow (the '018 patent) which is incorporated herein by reference. The '018 patent describes a readily dissolvable carrier that comprises a drug, an interim skeletal structure of a water soluble, hydratable gel or foam forming material, preferably a proteinaceous material.

The above formulations are given by way of example and other rapidly dissolving formulations will be apparent to those of skill in the art.

EXAMPLE 2

Bioavailability of Phentolamine Mesylate as a Rapidly Dissolving, Orally Administered Formulation Preliminary studies were conducted to compare the bioavailability of a single 40 mg dose of phentolamine mesylate when administered in the form of an orally administered rapidly dissolving tablet, with the bioavailability of phentolamine mesylate when orally administered in a standard release hard tablet.

Rapidly dissolving tablets containing 40 mg of phentolamine mesylate were prepared as described in Table 1. Standard release hard tablets containing 40 mg of phentolamine mesylate were prepared as follows:

TABLE 2

Standard Release Hard Tablet

|  | mg/tablet |
|---|---|
| Phentolamine Mesylate, USP | 40 |
| Silicon Dioxide, NF | 8 |
| Stearic Acid, NF | 4 |
| Dicalcium Phosphate Dibasic, USP | 228 |
| Microcrystalline Cellulose, NF | 120 |
| Total Tablet Weight | 400 |

Tablets were formed by direct compression. Physical characteristics of tablets prepared according to Table 2 include a hardness of 11.5 Kp, average tablet thickness of 0.16 inches, and an average disintegration time of about 26.33 minutes.

In preliminary studies, a single dose of 40 mg of phentolamine either in the rapidly dissolving tablet formulation or in the standard release hard tablet were administered to a group of volunteers.

Five (5) ml blood samples were collected from each individual at pre-dose and at 0.25, 0.50, 0.75, 1.00, 1.5 and 2 hours after administration of the formulation and the plasma level of phentolamine was determined using gas chromatography with electron capture detection as follows.

Phentolamine (CIBA GEIGY AG) and an internal standard, BA11038 (CIBA GEIGY AG) were extracted from alkalinized human heparinized plasma with 5 % isopropyl alcohol in toluene. The compounds of interest were back extracted from the organic layer with an acid solution (e.g., 0.05 M sulfonic acid), alkalinized again, and extracted with 5% isopropyl alcohol in toluene. Organic solvent was then evaporated and the dried extracts were reconstituted with hexane and derivatized with heptafluorobutyrylimidazole. The extracts were then washed and reconstituted with hexane. Extracts were then analyzed by injection into a gas chromatograph equipped with a DB-5 wide bore capillary column and an electron capture detector. The linear range of phentolamine concentration by this method was 5–400 ng/ml and the lower limit of accurate quantitation was 5 ng/ml. Levels of phentolamine were determined by comparison to a standard curve generated using known concentrations of phentolamine in solution processed using the procedure described above.

Table 3 sets out the plasma phentolamine concentration in volunteers receiving a 40 mg dose of phentolamine mesylate in a standard release hard tablet formulation shown in Table 2 at various times after administration.

TABLE 3

Individual and Mean Plasma Phentolamine Concentrations (ng/ml) After Administration of 40 mg Phentolamine Mesylate in a Standard Release Hard Tablet

| VOL | 0.25 hr | 0.50 hr | 0.75 hr | 1.00 hr | 1.50 hr | 2.00 hr |
|---|---|---|---|---|---|---|
| 1 | <5.0 | <5.0 | <5.0 | <5.0 | <5.0 | <5.0 |
| 2 | <5.0 | <5.0 | <5.0 | <5.0 | <5.0 | 8.3 |
| 3 | <5.0 | <5.0 | <5.0 | <5.0 | <5.0 | <5.0 |
| MEAN | 0.0 | 0.0 | 0.0 | 0.0 | 0.0 | 2.8 |
| STD. DEV. | 0.0 | 0.0 | 0.0 | 0.0 | 0.0 | 4.8 |
| C.V. (%) | 0 | 0 | 0 | 0 | 0 | 171 |
| S.E.M. | 0.0 | 0.0 | 0.0 | 0.0 | 0.0 | 2.8 |
| N | 3 | 3 | 3 | 3 | 3 | 3 |
| MIN | <5.0 | <5.0 | <5.0 | <5.0 | <5.0 | <5.0 |
| MAX | <5.0 | <5.0 | <5.0 | <5.0 | <5.0 | 8.3 |

As can be seen in Table 3, quantifiable levels of phentolamine were detected in only one of the three volunteers tested and were detected only at 2 hours after administration of the tablet.

However, as can be seen in Table 4 below, when the same volunteers were given a 40 mg dose of phentolamine mesylate in the rapidly dissolving tablet formulation shown in Table 1, quantifiable levels of phentolamine were detected in plasma as early as 0.25 hours after administration with a peak plasma level occurring between 0.5 hours and 0.75 hours after administration while falling below quantifiable levels between 1.5 hours and 2.0 hours after administration.

TABLE 4

Individual and Mean Plasma Phentolamine Concentrations (ng/ml) After Administration of 40 mg Phentolamine Mesylate in Rapidly Dissolving Tablet

| Volunteer | 0.25 hr | 0.50 hr | 0.75 hr | 1.00 hr | 1.50 hr | 2.00 hr |
|---|---|---|---|---|---|---|
| 1 | 14.0 | 22.6 | 17.9 | 13.7 | 6.2 | <5.0 |
| 2 | 11.2 | 15.9 | 14.7 | 12.6 | 6.6 | <5.0 |
| 3 | 13.7 | 13.2 | 10.3 | 9.9 | 7.2 | <5.0 |
| MEAN | 13.0 | 17.2 | 14.3 | 12.1 | 6.7 | 0.0 |
| STD. DEV. | 1.5 | 4.8 | 3.8 | 2.0 | 0.5 | 0.0 |
| C.V. (%) | 11.5 | 27.9 | 26.6 | 16.5 | 7.5 | 0 |
| S.E.M. | 0.9 | 2.8 | 2.2 | 1.2 | 0.3 | 0.0 |
| N | 3 | 3 | 3 | 3 | 3 | 3 |
| MIN | 11.2 | 13.2 | 10.3 | 9.9 | 6.2 | <5.0 |
| MAX | 14.0 | 22.6 | 17.9 | 13.7 | 7.2 | <5.0 |

In view of the data shown above that demonstrating that the rapidly dissolving oral formulation of phentolamine mesylate allows more rapid absorption of phentolamine mesylate into the blood stream than the standard release oral formulations, a more extensive study of bioavailability of several dosage levels of phentolamine mesylate administered in the rapidly dissolving oral formulation described above (40 mg phentolamine mesylate) were conducted. The formulations were prepared as follows:

TABLE 5

|  | mg/tablet |
|---|---|
| Phentolamine Mesylate, USP | 20 |
| Silicon Dioxide, NF | 8 |
| Stearic Acid, NF | 4 |
| Lactose, NF | 232 |
| Microcrystalline Cellulose, NF | 120 |
| Croscarmellose Sodium, NF | 16 |
| Total Tablet Weight | 400 |

TABLE 6

|  | mg/tablet |
|---|---|
| Phentolamine Mesylate, USP | 60 |
| Silicon Dioxide, NF | 8 |
| Stearic Acid, NF | 4 |
| Lactose, NF | 192 |
| Microcrystalline Cellulose, NF | 120 |
| Croscarmellose Sodium, NF | 16 |
| Total Tablet Weight | 400 |

After mixing of the ingredients, tablets were prepared by direct compression. Physical characteristics of the tablets prepared according to Tables 5 and 6 were very similar to those described for tablets prepared according to Table 1.

In this study, seven male subjects were selected based on medical history and physical examination. All patients had an impotence of organic etiology with a duration of less than 3–4 years.

In this study, subject males were given one of the above-indicated formulations of phentolamine mesylate in the indicated doses. Five milliliters of blood were collected from each patient at pre-dose and 0.083, 0.125, 0.167, 0.250, 0.50, 0.750, 1.0, 1.5, 2.0, 4.0, 6.0, and 8 hours following the dose and the plasma level of phentolamine was measured as described above.

Tables 7, 8, and 9 show the results of these studies.

Table 7 illustrates the plasma level of phentolamine mesylate after administration of a 20 mg dose of drug in the rapidly dissolving oral tablet formulation as shown in Table 5.

TABLE 7

Individual and Mean Plasma Phentolamine Concentrations (ng/mL) for Phentolamine Mesylate 20 mg Rapidly Dissolving Tablet

| VOLN | 0.000 hr | 0.083 hr | 0.125 hr | 0.167 hr | 0.250 hr | 0.500 hr | 0.750 hr | 1.000 hr | 1.500 hr | 2.000 hr | 4.000 hr | 6.000 hr | 8.000 hr |
|---|---|---|---|---|---|---|---|---|---|---|---|---|---|
| 1 | <5.0 | <5.0 | <5.0 | <5.0 | <5.0 | 6.7 | 9.6 | 11.4 | 7.8 | 6.2 | <5.0 | <5.0 | <5.0 |
| 2 | <5.0 | <5.0 | <5.0 | <5.0 | <5.0 | 8.1 | 6.0 | <5.0 | 5.9 | <5.0 | <5.0 | <5.0 | <5.0 |
| 3 | <5.0 | <5.0 | <5.0 | <5.0 | <5.0 | <5.0 | 9.0 | 9.1 | <5.0 | <5.0 | <5.0 | <5.0 | <5.0 |
| 4 | <5.0 | <5.0 | <5.0 | <5.0 | <5.0 | <5.0 | <5.0 | <5.0 | 7.7 | <5.0 | <5.0 | <5.0 | <5.0 |
| 5 | <5.0 | <5.0 | <5.0 | <5.0 | 8.2 | 6.6 | <5.0 | <5.0 | <5.0 | <5.0 | <5.0 | <5.0 | <5.0 |
| 6 | <5.0 | <5.0 | <5.0 | <5.0 | <5.0 | <5.0 | <5.0 | <5.0 | 7.1 | <5.0 | <5.0 | <5.0 | <5.0 |
| 7 | <5.0 | <5.0 | <5.0 | <5.0 | 10.3 | 16.7 | 10.9 | 7.2 | <5.0 | <5.0 | <5.0 | <5.0 | <5.0 |
| MEAN | 0.0 | 0.0 | 0.0 | 0.0 | 2.6 | 5.4 | 5.1 | 4.0 | 4.1 | 0.9 | 0.0 | 0.0 | 0.0 |
| STD. DEV. | 0.0 | 0.0 | 0.0 | 0.0 | 4.6 | 6.1 | 5.0 | 5.1 | 3.9 | 2.3 | 0.0 | 0.0 | 0.0 |
| C.V. (%) | 0 | 0 | 0 | 0 | 177 | 113 | 98.0 | 128 | 95.1 | 256 | 0 | 0 | 0 |
| S.E.M. | 0.0 | 0.0 | 0.0 | 0.0 | 1.7 | 2.3 | 1.9 | 1.9 | 1.5 | 0.9 | 0.0 | 0.0 | 0.0 |
| N | 7 | 7 | 7 | 7 | 7 | 7 | 7 | 7 | 7 | 7 | 7 | 7 | 7 |
| MIN | <5.0 | <5.0 | <5.0 | <5.0 | <5.0 | <5.0 | <5.0 | <5.0 | <5.0 | <5.0 | <5.0 | <5.0 | <5.0 |
| MAX | <5.0 | <5.0 | <5.0 | <5.0 | 10.3 | 16.7 | 10.9 | 11.4 | 7.8 | 6.2 | <5.0 | <5.0 | <5.0 |

As seen in Table 7, mean plasma phentolamine levels peak at about 5.4 ng/ml with the peak occurring between 0.25 hours and 0.50 hours, with a subsequent fall off in phentolamine level beginning between 0.50 hours and 0.75 hours.

Table 8 illustrates mean plasma levels of phentolamine after administration of a 40 mg dose in the rapidly dissolving oral formulation shown in Table 1.

TABLE 8

Individual and Mean Plasma Phentolamine Concentrations (ng/mL) for Phentolamine Mesylate 40 mg Tablet

| VOLN | 0.000 hr | 0.083 hr | 0.125 hr | 0.167 hr | 0.250 hr | 0.500 hr | 0.750 hr | 1.000 hr | 1.500 hr | 2.000 hr | 4.000 hr | 6.000 hr | 8.000 hr |
|---|---|---|---|---|---|---|---|---|---|---|---|---|---|
| 1 | <5.0 | <5.0 | <5.0 | <5.0 | 8.2 | 38.2 | 25.9 | 16.3 | 11.6 | 8.7 | 6.3 | <5.0 | <5.0 |
| 2 | <5.0 | <5.0 | <5.0 | 6.1 | 13.0 | 20.1 | 13.5 | 10.5 | 10.0 | 7.7 | <5.0 | <5.0 | <5.0 |

TABLE 8-continued

Individual and Mean Plasma Phentolamine Concentrations (ng/mL)
for Phentolamine Mesylate 40 mg Tablet

| VOLN | 0.000 hr | 0.083 hr | 0.125 hr | 0.167 hr | 0.250 hr | 0.500 hr | 0.750 hr | 1.000 hr | 1.500 hr | 2.000 hr | 4.000 hr | 6.000 hr | 8.000 hr |
|---|---|---|---|---|---|---|---|---|---|---|---|---|---|
| 3 | <5.0 | <5.0 | <5.0 | <5.0 | 8.0 | 20.6 | 15.9 | 14.3 | 13.7 | 9.6 | <5.0 | <5.0 | <5.0 |
| 4 | <5.0 | <5.0 | 5.6 | 5.4 | 8.2 | 11.8 | 17.9 | 15.3 | 10.6 | 9.2 | 5.3 | <5.0 | <5.0 |
| 5 | <5.0 | <5.0 | <5.0 | <5.0 | <5.0 | <5.0 | <5.0 | <5.0 | 9.7 | 9.3 | <5.0 | <5.0 | <5.0 |
| 6 | <5.0 | <5.0 | <5.0 | <5.0 | <5.0 | <5.0 | 11.0 | 15.1 | 17.0 | 11.4 | <5.0 | <5.0 | <5.0 |
| 7 | <5.0 | <5.0 | <5.0 | <5.0 | 6.8 | 26.2 | NS | 20.0 | 14.4 | 10.8 | <5.0 | <5.0 | <5.0 |
| MEAN | 0.0 | 0.0 | 0.8 | 1.6 | 6.3 | 16.7 | 14.0 | 13.1 | 12.4 | 9.5 | 1.7 | 0.0 | 0.0 |
| STD. DEV. | 0.0 | 0.0 | 2.1 | 2.8 | 4.7 | 13.9 | 8.6 | 6.4 | 2.7 | 1.2 | 2.8 | 0.0 | 0.0 |
| C.V. (%) | 0 | 0 | 263 | 175 | 74.6 | 83.2 | 61.4 | 48.9 | 21.8 | 12.6 | 165 | 0 | 0 |
| S.E.M. | 0.0 | 0.0 | 0.8 | 1.1 | 1.8 | 5.3 | 3.5 | 2.4 | 1.0 | 0.5 | 1.1 | 0.0 | 0.0 |
| N | 7 | 7 | 7 | 7 | 7 | 7 | 6 | 7 | 7 | 7 | 7 | 7 | 7 |
| MIN | <5.0 | <5.0 | <5.0 | <5.0 | <5.0 | <5.0 | <5.0 | <5.0 | 9.7 | 7.7 | <5.0 | <5.0 | <5.0 |
| MAX | <5.0 | <5.0 | 5.6 | 6.1 | 13.0 | 38.2 | 25.9 | 20.0 | 17.0 | 11.4 | 6.3 | <5.0 | <5.0 |

These data show that the mean plasma levels of phentolamine peak at about 16.7 ng/ml with the peak occurring at around 0.5 hours after administration while quantifiable levels of drug were maintained for as long as 2 hours after administration with two patients showing quantifiable levels for as long as 4 hours after administration.

Table 9 illustrates individual and mean plasma phentolamine concentrations in plasma after administration of a 60 mg dose of phentolamine mesylate in the rapidly dissolving oral formulation shown in Table 6.

TABLE 9

Individual and Mean Plasma Phentolamine Concentrations (ng/mL)
for Phentolamine Mesylate 60 mg Tablet

| VOLN | 0.000 hr | 0.083 hr | 0.125 hr | 0.167 hr | 0.250 hr | 0.500 hr | 0.750 hr | 1.000 hr | 1.500 hr | 2.000 hr | 4.000 hr | 6.000 hr | 8.000 hr |
|---|---|---|---|---|---|---|---|---|---|---|---|---|---|
| 1 | <5.0 | <5.0 | <5.0 | <5.0 | 8.1 | 20.1 | 15.5 | 13.4 | 16.3 | 18.6 | 12.4 | 5.3 | <5.0 |
| 2 | <5.0 | <5.0 | <5.0 | <5.0 | <5.0 | 42.2 | 41.0 | 25.1 | 17.2 | 13.7 | 8.1 | <5.0 | <5.0 |
| 3 | <5.0 | <5.0 | <5.0 | <5.0 | <5.0 | 15.4 | 38.2 | 43.8 | 27.7 | 16.3 | 7.1 | <5.0 | <5.0 |
| 4 | <5.0 | <5.0 | <5.0 | <5.0 | <5.0 | <5.0 | 13.7 | 32.1 | 23.5 | 14.6 | 8.0 | <5.0 | <5.0 |
| 5 | <5.0 | <5.0 | <5.0 | <5.0 | <5.0 | 20.1 | 18.4 | 12.2 | 10.3 | 6.7 | <5.0 | <5.0 | <5.0 |
| 6 | <5.0 | <5.0 | <5.0 | 5.7 | 11.8 | 12.8 | 21.2 | 17.4 | 25.2 | 13.3 | 5.8 | <5.0 | <5.0 |
| 7 | <5.0 | <5.0 | <5.0 | 5.3 | 24.6 | 49.7 | 46.1 | 37.7 | 25.3 | 16.7 | 8.3 | <5.0 | <5.0 |
| MEAN | 0.0 | 0.0 | 0.0 | 1.6 | 6.4 | 22.9 | 27.7 | 26.0 | 20.8 | 14.3 | 7.1 | 0.8 | 0.0 |
| STD. DEV. | 0.0 | 0.0 | 0.0 | 2.7 | 9.4 | 17.3 | 13.5 | 12.3 | 6.3 | 3.8 | 3.7 | 2.0 | 0.0 |
| C.V. (%) | 0 | 0 | 0 | 169 | 147 | 75.5 | 48.7 | 47.3 | 30.3 | 26.6 | 52.1 | 250 | 0 |
| S.E.M. | 0.0 | 0.0 | 0.0 | 1.0 | 3.6 | 6.5 | 5.1 | 4.6 | 2.4 | 1.4 | 1.4 | 0.8 | 0.0 |
| N | 7 | 7 | 7 | 7 | 7 | 7 | 7 | 7 | 7 | 7 | 7 | 7 | 7 |
| MIN | <5.0 | <5.0 | <5.0 | <5.0 | <5.0 | <5.0 | 13.7 | 12.2 | 10.3 | 6.7 | <5.0 | <5.0 | <5.0 |
| MAX | <5.0 | <5.0 | <5.0 | 5.7 | 24.6 | 49.7 | 46.1 | 43.8 | 27.7 | 18.6 | 12.4 | 5.3 | <5.0 |

The results in Table 9 show that near the plasma levels in patients receiving 60 mg of phentolamine in a rapidly dissolving oral formulation peaked at about 2.27 ng/ml with the peak occurring at around 0.75 hours after administration while quantifiable levels of drug remained in the plasma for at least 4 hours after administration.

While the studies described above were conducted using a rapidly dissolving formulation, other formulations that allow rapid absorption of an active vasodilator agent and corresponding improvement in erectile ability are within the scope of the present invention. For example, the present invention also includes a chewable tablet formulation shown in Table 10.

TABLE 10

|  | mg/tablet |
|---|---|
| Phentolamine Mesylate, USP | 40 |
| Silicon Dioxide, NP | 12 |
| Stearic Acid, NF | 12 |
| Lactose, NF | 100 |
| Sweetrex | 348 |
| Aspartame | 40 |
| ProSweet | 8 |
| Peppermint Flavor #860-172 | 40 |
| Total Tablet Weight | 600 |

EXAMPLE 3

Effect of the Administration of Rapidly Dissolving Oral Formulation of Phentolamine Mesylate on Male Erectile Ability In order to test the ability of a rapidly dissolving oral formulation of phentolamine mesylate on erectile ability, a single blind trial was conducted.

All patients had impotence of organic etiology. Patients were selected for inclusion in the trial based medical history and physical examination with a duration of impotence of less than 3–4 years. Each patient was given two tablets: a rapidly dissolving tablet containing 40 mg of phentolamine mesylate (see Table 1), and a placebo tablet lacking phentolamine mesylate.

Patients were asked to take one tablet 20 to 30 minutes before attempting coitus. One or more days after using the first tablet, the patients repeated the process with the second tablet.

Patients were advised not to consume alcohol prior to using the tablets and were told not to expect erection without sexual stimulation. Patients were told that either tablet might prove beneficial and were told to report results in terms of erection and vaginal penetration or failure to achieve an erection sufficient for vaginal penetration. Patients were also asked to report side effects. Results of this study are illustrated in Table 10.

TABLE 11

| Group | Tablet A (drug) | | Tablet B (placebo) | |
|---|---|---|---|---|
| | S | U | S | U |
| A | 2 | 2 | 0 | 4 |
| B | 1 | 3 | 0 | 4 |
| Total | 3 | 5 | 0 | 8 |

S = Erection sufficient for vaginal penetration
U = Erection Insufficient for vaginal penetration As can be seen in Table 11, 50% of patients in Group A who took the rapidly dissolving oral formulation were able to achieve erection sufficient for vaginal penetration within 30 minutes of administration of the drug while 33% of the patients in Group B had success. Also, as shown in Table 10, there were no placebo responders.

Although significant success was achieved using a 40 mg dose of phentolamine mesylate, it is expected that doses ranging from about 5 mg to about 100 mg of phentolamine will be useful in the practice of the present invention.

EXAMPLE 4

Vasoactive Agents Useful in Modulating the Human Sexual Response

A number of other vasoactive agents may be used in the practice of the present invention based on their demonstrated efficacy as vasodilators. Useful vasodilating drugs include those generally classified as α-adrenergic antagonists, sympathomimetic amines and those agents which exhibit direct relaxation of vascular smooth muscle.

Exemplary α-adrenergic antagonists include phentolamine hydrochloride, phentolamine mesylate, phenoxybenzamine, tolazoline, dibenamine, yohimbine, and others. Phentolamine mesylate is preferred in the practice of the present invention. An exemplary sympathomimetic amine contemplated for use in the method of the present invention is nylidrin although other sympathomimetic amines having vasodilating activity are also comprehended by the invention.

Nicotinic acid (or nicotinyl alcohol) has a direct vasodilating activity which is useful in the practice of the present invention. Papaverine is also non-specific smooth muscle relaxant which has vasodilating activity and has been used to treat male impotence by direct injection into the corpus cavernosum either alone or in combination with other drugs such as phentolamine.

Organic nitrates such as nitroglycerine and amyl nitrate also have pronounced vasodilating activity by virtue of their ability to relax vascular smooth muscle. Other vasoactive drugs of use in the practice of the present invention include but are not limited to thymoxamine, imipramine, verapamil, naftidrofuryl, isoxsuprine, and others.

In the practice of the present invention, these vasoactive agents are administered in rapidly dissolving orally administered formulation or other formulations such as troches, lozenges, chewable tablets, effervescent formulation, powders, solutions, and other formulations that provide for rapid delivery of the vasodilating agent to the systemic circulation and which provide the on demand of advantages of the present invention.

Appropriate doses of each vasoactive agents for each route of administration are readily determined by those of ordinary skill in the art. By way of illustration, in order to determine the appropriate dose of each of the vasodilating agents of the present invention, one of ordinary skill in the art may use as a starting point, the usual published dosage of the vasodilator. The usual oral doses for commercially available vasodilators can be found in the Physician's Desk Reference published annually by Medical Economic Data, Montvale, N.J., and in the available medical literature.

By way of example, Pavabid® oral papaverine hydrochloride is available from Marion Merrell Dow and is normally administered at 150 mg every 12 hours to achieve its vasodilating effects.

The oral dose of Calon® (verapamil hydrochloride) available from Searle is determined by titrating the individual patient with from 120 mg to about 240 mg of drug every 12 hours, the specific dose depending on the individual patient's response to the drug.

Yohimbine hydrochloride available as Daytohimbin® (Dayton Pharmaceuticals), Yocon® (Palisades Pharmaceuticals), and Yohimex® (Kramer) are all administered orally as 5.4 mg three times a day.

Imipramine hydrochloride is available as Tofranil® from Geigy and is administered orally 4 times a day for a total dose ranging from 50 mg to about 150 mg per day.

Imipramine pamoate, also available from Geigy is administered in oral maintenance doses of 150 mg/day.

Using the established oral dosages as starting points, the optimal dosage for the specific route of administration can be determined by measuring baseline arterial blood flow in genital circulation of the patient prior to administration of the drug using a doppler ultrasound velocimeter as described in Zorgniotti et al., PCT/US94/09048. Other methods such as thermography, plethysmography, radiometric or scintigraphic methods, and other methods well known in the art may also be utilized to assess blood flow in the genitalia. Having established base line blood flow, various dosages of the respective vasodilators may be administered using the formulations encompassed by the present invention and their effect on blood flow may be measured. The magnitude of the increase in blood flow necessary to modulate or enhance the sexual response in humans may vary from individual to individual, but is readily determined as described in Zorgniotti et al. PCT/US94/09048. In addition, individual patients may be titrated with various dosages of the respective vasodilators until the optimum dosage is determined.

Vascular flow studies may also be coupled with assessments of sexual responsiveness as evidenced by the improvement of erectile ability in response to sexual stimulation.

EXAMPLE 5

Modulation of the Female Sexual Response

As discussed above, there are striking parallels between the vascular anatomy of male and female genitalia and in the erectile response facilitated by this vasculature. In both males and females, the erectile response takes place when under physical or psychological stimulation, blood flow to the genitalia increases by virtue of relaxation of smooth muscles in the arteries serving the genitalia.

The methods and formulations of the present invention may be used to improve or enhance the erectile response in women whose sexual response is impaired as evidenced by diminished capacity to produce sufficient vaginal lubrication to facilitate comfortable penile penetration and by other symptoms of impaired sexual responsiveness that may be correlated with the erectile response.

As in the case of male sexual response, in the absence of any clinically diagnosed dysfunction in the female erectile response, the methods of the present invention may be used to enhance the normal female sexual response. The "on demand" aspect of the present invention will allow a more rapid response to sexual stimulation along with heightened sensation associated with excitement and plateau stages of the female sexual response by virtue of the increased blood flow to the tissues.

In practice, enhancement of the female sexual response using the methods of the present invention are carried in much the same way as those described for males as described above.

An effective vasodilating dose of a vasodilating agent is administered to a woman the formulations of the present invention. The e appropriate doses of the particular vasodilating agent may be readily determined using methods described in Example 4. The female response may be measured using methods described in Masters, W. H. and Johnson, V. E., *Human Sexual Response*, Little, Brown, and Co., Boston (1966) which is incorporated herein by reference. Methods for measuring blood flow, including doppler ultrasonic velocimetry, thermography using for example an isothermal blood flow transducer, radioscintigraphic methods, photoplethysmography may be used as well as other methods well known in the art. In addition, measuring the contraction of the distal ⅓ as is characteristic of the plateau phase of female sexual response of the vagina may be measured using methods and equipment well known in the art including but not limited to strain gauges or other devices for measuring muscular contraction or muscle tension.

In addition, enhanced sexual response may be measured in a more subjective manner by simply asking the female subject to describe any change in sensation brought about by administration of the vasodilator by the methods of the present invention. Appropriate placebo controls should also be conducted to ascertain whether or not the effort is directly attributable to the administration of the vasodilator.

Preferred embodiments of the present invention involves the administration of from about 5 mg to about 80 mg of phentolamine mesylate in a rapidly dissolving oral formulation of the present invention from about 1 minute to about 1 hour prior to, and in preparation for intercourse. However any of the vasodilating agents included within the scope of the present invention may be used.

While this invention has been described by way of preferred embodiments, the examples set out herein are not intended to limit the scope of the invention which contemplates the use of any pharmacologic vasodilating drug capable of absorption into the systemic circulation upon administration of the drug via an orally administered formulation capable of improving erectile ability on demand.

We claim:

1. A method of treating male impotence comprising orally ingesting a composition comprising a pharmaceutically acceptable carrier including a disintegrant and an amount of a phentolamine vasodilator or a pharmaceutically acceptable salt thereof, in a solvated form, including hemi-hydrate, or in an unsolvated form, effective to treat said male impotence within one hour prior to attempting sexual intercourse.

2. The method of claim 1 wherein the pharmaceutically acceptable salt of phentolamine is a salt prepared by contacting a free base of phentolamine with an organic or inorganic acid selected from the group of acids consisting of hydrochloric, hydrobromic, sulfuric, phosphoric, acetic, citric, oxalic, malonic, salicylic, malic, furmaric, succinic, ascorbic, maleic, methanesulfonic, and toluenesulfonic.

3. The method of claim 2 wherein the amount of a pharmaceutically acceptable phentolamine salt in the composition is from about 40 to about 80 mg.

4. The method of claim 2 wherein the amount of a pharmaceutically acceptable phentolamine salt in the composition is from about 5 to about 80 mg.

5. The method of any of claims 1, 2, 3 or 4 wherein said disintegrant is selected from the group consisting of croscarmellose sodium, potato starch, analgetic acid, sodium starch glycolate, crospovidone, and pregelatinized starch.

6. The method of claim 5 wherein the disintegrant is croscarmellose sodium.

7. The method of claim 5 wherein said composition is a tablet or capsule.

8. The method of claim 7 wherein said male impotence is treated by oral ingestion of said composition within one hour prior to attempting sexual intercourse and by sexual stimulation.

9. The method of claim 7 wherein said male impotence is treated by oral ingestion of said composition within 45 minutes prior to attempting sexual intercourse.

10. The method of claim 9 wherein said male impotence is treated by oral ingestion of said composition within 45 minutes prior to attempting sexual intercourse and by sexual stimulation.

11. The method of claim 7 wherein said male impotence is treated by oral ingestion of said composition within 30 minutes prior to attempting sexual intercourse.

12. The method of claim 11 wherein said male impotence is treated by oral ingestion of said composition within 30 minutes prior to sexual intercourse and by sexual stimulation.

13. The method of claim 5 wherein said male impotence is treated by oral ingestion of said composition within one hour prior to attempting sexual intercourse and by sexual stimulation.

14. The method of claim 5 wherein said male impotence is treated by oral ingestion of said composition within 45 minutes prior to attempting sexual intercourse.

15. The method of claim 14 wherein said male impotence is treated by oral ingestion of said composition within 45 minutes prior to attempting sexual intercourse and by sexual stimulation.

16. The method of claim 5 wherein said male impotence is treated by oral ingestion of said composition within 30 minutes prior to attempting sexual intercourse.

17. The method of claim 16 wherein said male impotence is treated by oral ingestion of said composition within 30 minutes prior to sexual intercourse and by sexual stimulation.

18. The method of any of claims 1, 2, 3, 4 or 6 wherein said composition is a tablet or capsule.

19. The method of claim 18 wherein said male impotence is treated by oral ingestion of said composition within one hour prior to attempting sexual intercourse and by sexual stimulation.

20. The method of claim 18 wherein said male impotence is treated by oral ingestion of said composition within 45 minutes prior to attempting sexual intercourse.

21. The method of claim 20 wherein said male impotence is treated by oral ingestion of said composition within 45 minutes prior to attempting sexual intercourse and by sexual stimulation.

22. The method of claim 18 wherein said male impotence is treated by oral ingestion of said composition within 30 minutes prior to attempting sexual intercourse.

23. The method of claim 22 wherein said male impotence is treated by oral ingestion of said composition within 30 minutes prior to sexual intercourse and by sexual stimulation.

24. A method for treating male impotence comprising oral ingestion of a composition comprising a pharmaceutically acceptable carrier including a disintegrant and an amount of a phentolamine vasodilator or a pharmaceutically acceptable salt thereof, in a solvated form, including hemi-hydrate, or in an unsolvated form, effective to improve erectile ability within one hour of oral ingestion of said composition.

25. The method of claim 24 wherein the pharmaceutically acceptable salt of phentolamine is a salt prepared by contacting a free base of phentolamine with an organic or inorganic acid selected from the group of acids consisting of hydrochloric, hydrobromic, sulfuric, phosphoric, acetic, citric, oxalic, malonic, salicylic, malic, furmaric, succinic, ascorbic, maleic, methanesulfonic, and toluenesulfonic.

26. The method of claim 25 wherein the amount of a pharmaceutically acceptable phentolamine salt is from about 5 to about 80 mg.

27. The method of claim 25 wherein the amount of a pharmaceutically acceptable phentolamine salt is from about 40 to about 80 mg.

28. The method of any of claims 24, 25, 26 or 27 wherein said disintegrant is selected from the group consisting of croscarmellose sodium, potato starch, analgetic acid, sodium starch glycolate, crospovidone, and pregelatinized starch.

29. The method of claim 28 wherein the disintegrant is croscarmellose sodium.

30. The method of any of claims 24, 25, 26 or 27 or 29 wherein said composition is a tablet or capsule.

31. The method of claim 30 wherein said improvement in erectile ability is within one hour of oral ingestion of said composition and in response to sexual stimulation.

32. The method of claim 30 wherein said improvement in erectile ability is within 45 minutes of oral ingestion of said composition.

33. The method of claim 32 wherein said improvement in erectile ability is within 45 minutes of oral ingestion of said composition and in response to sexual stimulation.

34. The method of claim 30 wherein said improvement in erectile ability is within 30 minutes of oral ingestion of said composition.

35. The method of claim 34 wherein said improvement in erectile ability is within 30 minutes of oral ingestion of said composition and in response to sexual stimulation.

36. The method of claim 29 wherein said improvement in erectile ability is within one hour of oral ingestion of said composition and in response to sexual stimulation.

37. The method of claim 29 wherein said improvement in erectile ability is within 45 minutes of oral ingestion of said compound.

38. The method of claim 37 wherein said improvement in erectile ability is within 45 minutes of oral ingestion of said composition and in response to sexual stimulation.

39. The method of claim 29 wherein said improvement in erectile ability is within 30 minutes of oral ingestion of said composition.

40. The method of claim 39 wherein said improvement in erectile ability is within 30 minutes of oral ingestion of said composition and in response to sexual stimulation.

41. The method of claim 28 wherein said composition is a tablet or capsule.

42. The method of claim 41 wherein said improvement in erectile ability is within one hour of oral ingestion of said composition and in response to sexual stimulation.

43. The method of claim 41 wherein said improvement in erectile ability is within 45 minutes of oral ingestion of said composition.

44. The method of claim 43 wherein said improvement in erectile ability is within 45 minutes of oral ingestion of said composition and in response to sexual stimulation.

45. The method of claim 41 wherein said improvement in erectile ability is within 30 minutes of oral ingestion of said composition.

46. The method of claim 45 wherein said improvement in erectile ability is within 30 minutes of oral ingestion of said composition and in response to sexual stimulation.

47. The method of claim 28 wherein said improvement in erectile ability is within one hour of oral ingestion of said composition and in response to sexual stimulation.

48. The method of claim 28 wherein said improvement in erectile ability is within 45 minutes of oral ingestion of said compound.

49. The method of claim 48 wherein said improvement in erectile ability is within 45 minutes of oral ingestion of said composition and in response to sexual stimulation.

50. The method of claim 28 wherein said improvement in erectile ability is within 30 minutes of oral ingestion of said composition.

51. The method of claim 50 wherein said improvement in erectile ability is within 30 minutes of oral ingestion of said composition and in response to sexual stimulation.

52. A method for treating male impotence comprising oral ingestion of a tablet comprising a pharmaceutically acceptable carrier including a disintegrant and an amount of a phentolamine vasodilator or a pharmaceutically acceptable salt thereof, in a solvated form, including hemi-hydrate, or in an unsolvated form, effective to improve erectile ability within one hour of oral ingestion.

53. The method of claim 52 wherein the pharmaceutically acceptable salt of phentolamine is a salt prepared by contacting a free base of phentolamine with an organic or inorganic acid selected from the group of acids consisting of hydrochloric, hydrobromic, sulfuric, phosphoric, acetic, citric, oxalic, malonic, salicylic, malic, furmaric, succinic, ascorbic, maleic, methanesulfonic, and toluenesulfonic.

54. The method of claim 52 wherein the amount of a pharmaceutically acceptable phentolamine salt in the tablet is from about 5 to about 80 mg.

55. The method of claim 52 wherein the amount of a pharmaceutically acceptable phentolamine salt in the tablet is from about 40 to about 80 mg.

56. The method of any of claims 52, 53, 54 or 55 wherein said disintegrant is selected from the group consisting of croscarmellose sodium, potato starch, analgetic acid, sodium starch glycolate, crospovidone, and pregelatinized starch.

57. The method of claim 56 wherein the disintegrant is croscarmellose sodium.

58. The method of any of claims 52, 53, 54, 55 or 57 wherein said improvement in erectile ability is within one hour of oral ingestion of said composition and in response to sexual stimulation.

59. The method of claim 56 wherein said improvement in erectile ability is within one hour of oral ingestion of said composition and in response to sexual stimulation.

60. The method of any of claims 52, 53, 54, 55 or 57 wherein said improvement in erectile ability is within 45 minutes of oral ingestion of said composition.

61. The method of claim 60 wherein said improvement in erectile ability is within 45 minutes of oral ingestion of said composition and in response to sexual stimulation.

62. The method of claim 56 wherein said improvement in erectile ability is within 45 minutes of oral ingestion of said composition.

63. The method of claim 62 wherein said improvement in erectile ability is within 45 minutes of oral ingestion of said composition and in response to sexual stimulation.

64. The method of any of claims 52, 53, 54, 55 or 57 wherein said improvement in erectile ability is within 30 minutes of oral ingestion of said composition.

65. The method of claim 64 wherein said improvement in erectile ability is within 30 minutes of oral ingestion of said composition and in response to sexual stimulation.

66. The method of claim 56 wherein said improvement in erectile ability is within 30 minutes of oral ingestion of said composition.

67. The method of claim 66 wherein said improvement in erectile ability is within 30 minutes of oral ingestion of said composition and in response to sexual stimulation.

68. A method for treating male impotence comprising oral ingestion of a formulation comprising a pharmaceutically acceptable carrier and an amount of a phentolamine vasodilator or a pharmaceutically acceptable salt thereof, in a solvated form, including hemi-hydrate, or in an unsolvated form, effective to improve erectile ability within one hour of oral ingestion of said formulation.

69. The method of claim 68 wherein the pharmaceutically acceptable salt of phentolamine is a salt prepared by contacting a free base of phentolamine with an organic or inorganic acid selected from the group of acids consisting of hydrochloric, hydrobromic, sulfuric, phosphoric, acetic, citric, oxalic, malonic, salicylic, malic, furmaric, succinic, ascorbic, maleic, methanesulfonic, and toluenesulfonic.

70. The method of claim 69 wherein the amount of a pharmaceutically acceptable phentolamine salt in the composition is from about 5 to about 80 mg.

71. The method of claim 69 wherein the amount of a pharmaceutically acceptable phentolamine salt in the composition is from about 40 to about 80 mg.

72. The method of any of claims 68, 69, 70 or 71 wherein the formulation is selected from the group consisting of capsules, solutions, suspensions, emulsions, and powders.

73. The method of claim 72 wherein said improvement in erectile ability is within one hour of oral ingestion of said formulation and in response to sexual stimulation.

74. The method of claim 72 wherein said improvement in erectile ability occurs within 45 minutes of oral ingestion of said formulation.

75. The method of claim 74 wherein said improvement in erectile ability is within 45 minutes of oral ingestion of said formulation and in response to sexual stimulation.

76. The method of claim 72 wherein said improvement in erectile ability occurs within 30 minutes of oral ingestion of said formulation.

77. The method of claim 76 wherein said improvement in erectile ability occurs within 30 minutes of oral ingestion of said formulation and in response to sexual stimulation.

78. The method of claim 68 wherein the formulation is a capsule.

79. The method of any of claims 68, 69, 70, 71 or 78 wherein said improvement in erectile ability is within one hour of oral ingestion of said formulation and in response to sexual stimulation.

80. The method of claim 78 wherein said improvement in erectile ability is within 45 minutes of oral ingestion of said formulation and in response to sexual stimulation.

81. The method of claim 78 wherein said improvement in erectile ability occurs within 30 minutes of oral ingestion of said formulation and in response to sexual stimulation.

82. The method of any of claims 68, 69, 70, 71 or 78 wherein said improvement in erectile ability occurs within 45 minutes of oral ingestion of said formulation.

83. The method of claim 82 wherein said improvement in erectile ability is within 45 minutes of oral ingestion of said formulation and in response to sexual stimulation.

84. The method of any of claims 68, 69, 70, 71 or 78 wherein said improvement in erectile ability occurs within 30 minutes of oral ingestion of said formulation.

85. The method of claim 84 wherein said improvement in erectile ability occurs within 30 minutes of oral ingestion of said formulation and in response to sexual stimulation.

86. A method for treating male impotence comprising oral ingestion of a formulation comprising a pharmaceutically acceptable carrier and an effective amount of a phentolamine vasodilator or a pharmaceutically acceptable salt thereof, in a solvated form, including hemi-hydrate, or in an unsolvated form within one hour prior to attempting sexual intercourse.

87. The method of claim 86 wherein the pharmaceutically acceptable salt of phentolamine is a salt prepared by contacting a free base of phentolamine with an organic or inorganic acid selected from the group of acids consisting of hydrochloric, hydrobromic, sulfuric, phosphoric, acetic, citric, oxalic, malonic, salicylic, malic, furmaric, succinic, ascorbic, maleic, methanesulfonic, and toluenesulfonic.

88. The method of claim 87 wherein the amount of a pharmaceutically acceptable phentolamine salt in the composition is from about 5 to about 80 mg.

89. The method of claim 87 wherein the amount of a pharmaceutically acceptable phentolamine salt in the composition is from about 40 to about 80 mg.

90. The method of any of claims 86, 87, 88 or 89 wherein the formulation is selected from the group consisting of capsules, solutions, suspensions, emulsions and powders.

91. The method of claim 86 wherein the formulation is a capsule.

92. The method of any of claims 86, 87, 88, 89 or 91 wherein said male impotence is treated by oral ingestion of said compositions within one hour prior to attempting sexual intercourse and by sexual stimulation.

93. The method of claim 90 wherein said male impotence is treated by oral ingestion of said compositions within one hour prior to attempting sexual intercourse and by sexual stimulation.

94. The method of any of claims 86, 87, 88, 89 or 91 wherein said male impotence is treated by oral ingestion of said composition within 45 minutes prior to attempting sexual intercourse.

95. The method of claim 94 wherein said male impotence is treated by oral ingestion of said composition within 45 minutes prior to attempting sexual intercourse and by sexual stimulation.

96. The method of claim 90 wherein said male impotence is treated by oral ingestion of said composition within 45 minutes prior to attempting sexual intercourse.

97. The method of claim 96 wherein said male impotence is treated by oral ingestion of said composition within 45 minutes prior to attempting sexual intercourse and by sexual stimulation.

98. The method of claim 90 wherein said male impotence is treated by oral ingestion of said composition within 30 minutes prior to attempting sexual intercourse.

99. The method of claim 98 wherein said male impotence is treated by oral ingestion of said composition within 30 minutes prior to attempting sexual intercourse and by sexual stimulation.

100. The method of any of claims 86, 87, 88, 89 or 91 wherein said male impotence is treated by oral ingestion of said composition within 30 minutes prior to attempting sexual intercourse.

101. The method of claim 100 wherein said male impotence is treated by oral ingestion of said composition within 30 minutes prior to attempting sexual intercourse and by sexual stimulation.

* * * * *